United States Patent [19]
Perrault

[11] Patent Number: 5,470,625
[45] Date of Patent: Nov. 28, 1995

[54] STRAND-OF-BEADS WOUND PACKING PRODUCT

[75] Inventor: James J. Perrault, Brooklyn Center, Minn.

[73] Assignee: Medtronic, Inc., Minneapolis, Minn.

[21] Appl. No.: 171,316

[22] Filed: Dec. 21, 1993

[51] Int. Cl.$^6$ .............................. B32B 3/16; C08G 75/20; B65D 81/24; A61B 19/02

[52] U.S. Cl. .......................... 428/48; 528/385; 528/386; 602/48; 602/49; 602/51; 602/56; 607/114; 607/118; 206/440; 206/210; 206/441

[58] Field of Search ..................................... 528/385, 386; 428/48; 602/48, 49, 51, 56; 607/114, 118; 206/440, 441, 210

[56] References Cited

U.S. PATENT DOCUMENTS

| | | | |
|---|---|---|---|
| 4,593,053 | 6/1986 | Jevne | 524/503 |
| 4,867,821 | 9/1989 | Morgan | 156/152 |
| 4,930,500 | 6/1990 | Morgan | 128/156 |
| 5,002,792 | 3/1991 | Vegoe | 427/2 |

*Primary Examiner*—George F. Lesmes
*Assistant Examiner*—Kathryne E. Shelborne
*Attorney, Agent, or Firm*—Richard H. Kosakowski; Holland & Associates

[57] ABSTRACT

An elongated segmented wound packing product comprised of individual linked segments of hydrogel enclosed within a liquid permeable pliable material, the individual segments being connected in a strand-of-beads like configuration.

10 Claims, 1 Drawing Sheet

0

STRAND-OF-BEADS WOUND PACKING PRODUCT

BACKGROUND OF THE INVENTION

This invention relates to packing material for deep wounds, particularly a packing product utilizing hydrogel. Hydrogel compositions are the absorbent wound packing material of choice. However, packing products for deep wounds presently are comprised either of thin strips of absorbent material or hydrogel beads that swell and are later removed from the wound by irrigation. Hydrogel beads do not pack tightly in a wound, often leak out and their subsequent removal by irrigation is messy and often incomplete.

The wound packing product of this invention is constructed and arranged to allow hydrogel or other absorbent material to be packed tightly into the wound shape without leakage and with easy and complete removal with tweezers.

SUMMARY OF THE INVENTION

In accordance with this invention, a hydrogel or other absorbent material is encased in a liquid permeable, biocompatible material in a segmented fashion similar to a string of "sausage links", termed herein "strand-of-beads".

Such a product construction and arrangement allows the absorbent material to be packed readily into the shape of the wound, it allows for a unique and convenient presentation and removal of the absorbent material from the wound while containing same and avoiding unnecessary irrigation. Also, the absorption and delivery of therapeutic agents by means of the absorbent material can be controlled by the porosity of the encasing liquid permeable material.

DETAILED DESCRIPTION OF THE INVENTION

As already indicated, a hydrogel or other absorbent material is typically used as a wound packing material to absorb wound exudate. In accordance with this invention the absorbent material, preferably a hydrogel, is enclosed in a segmented but interconnected, highly flexible liquid permeable material, preferably a fabric, which allows the hydrogel to be tightly packed into a wound cavity and yet easily removed. Since the hydrogel is sealed within the fabric it can be cut to lengths to fit wounds of varying size.

The closest prior art is believed to be a rope-like product, manufactured and sold by Johnson & Johnson Medical, Inc., which does not pack well.

Figure 1:
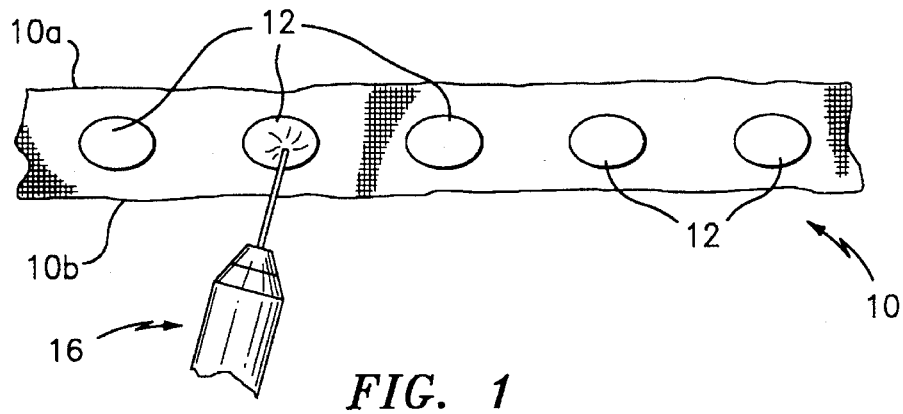
FIG. 1 is a top plan view of the invention and it illustrates a method of preparing the wound packing product of the invention.
Figure 2:
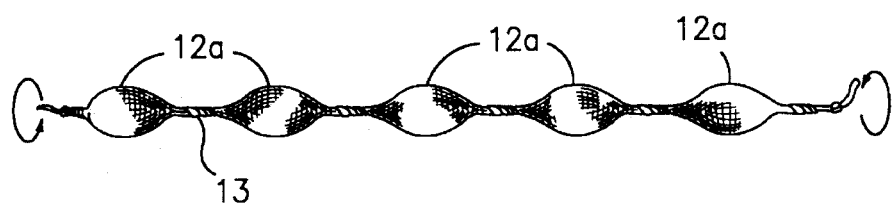
FIG. 2 is a top plan view thereof showing the concealing method of the gel tablets with the fabric.

Referring now to FIGS. 1 and 2, a method of preparing the wound packing product of the invention will be described in connection with one embodiment thereof. FIG. 1 shows an elongated sheet of liquid permeable material generally designated 10 and a series of discrete individual quantities of an absorbent hydrogel 12 deposited thereon. The sheet or strip 10 may be as long as desired and will include a plurality of discrete quantities of absorbent material.

The absorbent hydrogel will preferably be of the type described in U.S. Pat. No. 4,593,053, the entire content of which is incorporated herein by reference. These hydrogels are of the hot melt type as is fully described in U.S. Pat. No. 5,002,792, the entire content of which is incorporated herein by reference. Such hydrogels may be heated and extruded or injected in discrete quantities as shown in FIG. 1.

Other materials may also be used, not necessarily of the hot melt type, such as calcium alginate, polyethylene oxide, hydrophilic urethane and polyvinylpyrrolidone, to name a few other hydrogels. Non-hydrogels may also be used as the absorbent material. For example, sponge-like materials available from Avitar, Inc., of Cantor, Mass. under the trademark Hydrosorb™ may be used. Foam-like materials available from Acme United Corporation, Medical Products Division, of Fairfield, Conn. 0640, under the trademark Lyofoam® may also be used. This is a specially treated polyurethane. Various gauze materials as are known in the art for absorbent packing, karaya gum and hydrocolloid powder or granules may be used also.

The sheet or strip material 10 is preferably of a cotton/lycra net-like fabric such as is available as finger dressings from Deroyal Industries, Inc., of Powell, Tenn. 37849-4703, or a polyester/lycra net-like fabric available from Balfour Healthcare of Greensboro, N.C., 27417-7077. Alternatively, polyester, fluoropolymer, urethane, and cellulose materials may be used. One may even use wound packing gauze strips such as Johnson & Johnson NU GAUZE™ packing strips for this purpose.

Knitted and woven materials and net-like materials of the aforementioned materials may be controlled with respect to porosity by controlling the knitting or weaving pattern (tight to loose) or in the case of elastomer materials by controlling permeability.

The top and bottom edges of sheet 10 (10a and 10b, respectively) are overlapped to enclose the bodies 12 of hydrogel or other absorbent material. Depending on the material used for strip 10, it may then be heat sealed, ultrasonically welded, knotted or tied or twisted into a string of segmented sausage-like links 12a as shown in FIG. 2. As a result, carrier strip 10 is utilized to provide the segmented continuous linked configuration shown in FIG. 2, which is constructed and arranged to provide an elongate series of individual discrete segments of absorbent material enclosed in the pliable material, yet linked in an elongate configuration for convenience of use.

Figure 3:
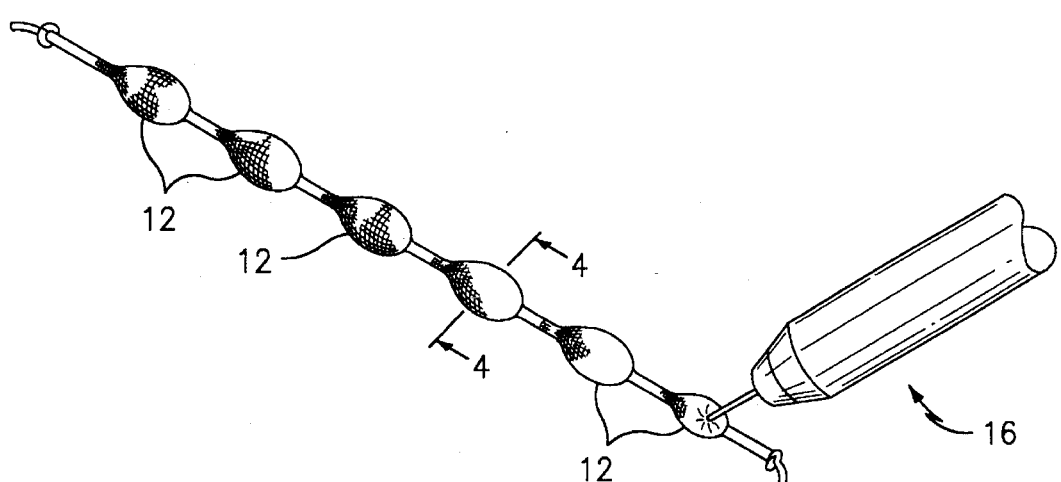
FIG. 3 is a perspective view thereof illustrating the developing of gel tablets within a tubular fabric.
Figure 4:
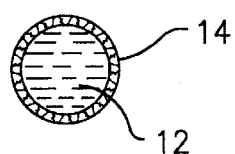
FIG. 4 is a cross sectional view thereof taken along line 4—4 in FIG. 3 showing the configuration of the subject.

In a more preferred form of manufacture, as shown in FIGS. 3 and 4, material 10 is provided in a tubular configuration 14 and the absorbent material 12 is injected through openings in the material or an injector needle is used to pierce the material at discrete intervals, depositing spaced quantities of absorbent material therein. This is shown at 16. The most preferred method involves the tying of spaced knots 18 in the tubular material and placement of absorbent material 12 within the tube at intervals between the knots. This arrangement can be seen in FIG. 3 with knots 18 between absorbent bodies 12.

In another embodiment of the invention, (not shown) the strands-of-beads arrangement may be used to exude rather than absorb. For example, the gel 12 can be presoaked in a therapeutic agent such as hypertonic saline solution or an antibiotic or the like. The strand may then be placed on the body as desired and allowed to exude the absorbed agent. In the case of hypertonic saline solution, the strand would be useful for debridement of scarring.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A wound packing product comprised of a pliable liquid permeable material enclosing an absorptive component in a continuous elongate series of individual discrete segments arranged in an elongate savage-like linked configuration.

2. The product of claim 1 wherein the absorptive component is comprised of a hydrogel.

3. The product of claim 1 wherein the liquid permeable material is selected from the group consisting of knitted, woven, net-like and permeable elastomeric material.

4. The product of claim 1 wherein the absorptive component includes therapeutic agents for delivery to the body.

5. The product of claim 1 wherein the liquid permeable material is of a predetermined permeability for the purpose of transport control.

6. The product of claim 1 wherein the permeable material is in the form of a tube.

7. The product of claim 6 wherein the tube is knotted at intervals along its length.

8. A wound packing product which comprises individual quantities of absorbent hydrogel located within an elongate carrier of pliable liquid permeable material segmented into a continuous savage-like linked configuration.

9. The product of claim 8 wherein the carrier is tubular in form.

10. The product of claim 9 wherein the tubular carrier is knotted at spaced intervals.

* * * * *